(12) United States Patent
Iglesia et al.

(10) Patent No.: US 7,507,855 B2
(45) Date of Patent: Mar. 24, 2009

(54) PROCESS FOR CARBONYLATION OF ALIPHATIC ALCOHOLS AND/OR ESTER DERIVATIVES THEREOF

(75) Inventors: Enrique Iglesia, Moraga, CA (US); John Glenn Sunley, East Yorkshire (GB); David John Law, East Yorkshire (GB); Aditya Bhan, Berkeley, CA (US)

(73) Assignees: The Regents of the University of California, Oakland, CA (US); BP Chemicals Ltd., Middlesex (GB)

( * ) Notice: Subject to any disclaimer, the term of this patent is extended or adjusted under 35 U.S.C. 154(b) by 179 days.

(21) Appl. No.: 11/639,437

(22) Filed: Dec. 15, 2006

(65) Prior Publication Data

US 2008/0146833 A1 Jun. 19, 2008

(51) Int. Cl.
C07C 67/36 (2006.01)
(52) U.S. Cl. ...................................... 560/232
(58) Field of Classification Search ........................ None
See application file for complete search history.

(56) References Cited

U.S. PATENT DOCUMENTS

| | | | |
|---|---|---|---|
| 3,130,007 A | 4/1964 | Breck | |
| 3,689,533 A | 9/1972 | Schultz | |
| 4,076,842 A | 2/1978 | Plank et al. | |
| 4,612,387 A | 9/1986 | Feitler | |
| 5,189,203 A | 2/1993 | Hansen et al. | |
| 5,218,140 A | 6/1993 | Wegman | |
| 5,286,900 A | 2/1994 | Hansen et al. | |
| 5,728,871 A | 3/1998 | Joensen et al. | |
| 5,763,654 A | 6/1998 | Jones et al. | |
| 6,130,355 A | 10/2000 | Jones | |
| 6,353,132 B1 | 3/2002 | Zoeller et al. | |
| 6,355,837 B1 | 3/2002 | Zoeller et al. | |
| 6,387,842 B1 | 5/2002 | Wegman et al. | |
| 6,521,783 B1 | 2/2003 | Wegman et al. | |
| 2003/0054951 A1 | 3/2003 | Zoeller et al. | |

FOREIGN PATENT DOCUMENTS

| | | |
|---|---|---|
| DE | 3606 169 A1 | 8/1987 |
| EP | 0 566 370 A2 | 10/1993 |
| EP | 0 566 371 A2 | 10/1993 |
| EP | 0 596 632 A1 | 5/1994 |
| GB | 1185453 | 3/1970 |
| GB | 1277242 | 6/1972 |
| WO | WO 2005/105720 | 11/2005 |

OTHER PUBLICATIONS

Baerlocher, C., et al; *The Atlas of Zoelite Framework Types*; 5th ed. Elsevier, Amsterdam, 2001—http://www.iza-structure.org/databases/.
Foster, M.D., et al; "A geometric solution to the largest-free-sphere problem in zeolite frameworks"; *Microporous and Mesoporous Materials* 90 (2006) pp. 32-38.
J. Phys. Chem. B., 109, 652-661 (2005), Zones, S.I. Darton, et al.
Vaughan, D.E.W, et al; Microporous Mesoporous Mat., 28, 233-239 (1999).
Barri, S.A.I., et al; "Theta-1"; Nature, 312, 533-534 (1984).
Martucci, A., et al; "Mazzite"; Microporous Mesoporous Mat., 63, 33-42 (2003).
Bhat, S.D., et al; "Zeolite L"; Microporous Mesoporous Mat., 76, 81-99 (2004).
Bhat, S.D., et al; J. Ind. Eng. Chem., vol. 10, No. 4 (2004), 636-644.
Ko, Y.S., et al; "offretite"; Zeolites 255-264, vol. 7 (1987), Howden M.G.
Makarova, M.A., et al; Journal of Catalysis, 1997, 172, (1), 170.
Ko, Y.S., et al; "Influence of Synthesis Parameters on the Morphology and Particle Size Distribution of Zeolite L"; *J. Ind. Eng. Chem.*, vol. 10, No. 4 (2004) pp. 636-644.
Bagno, Alessandro et al; "Superacid-Catalyzed Carbonylation of Methane, Methyl Halides, Methyl Alcohol, and Dimethyl Ether to Methyl Acetate and Acetic Acid"; 1990, *J. Org. Chem.*, vol. 55, pp. 4284-4289.
Ellis, Brian et al; "Heterogeneous Catalysts for the Direct, Halide-free Carbonylation of Methanol"; 1996, *11th International Congress on Catalysis*; pp. 771-779.
Fujimoto, Kaoru et al; "Vapor Phase Carbonylation of Methanol with Solid Acid Catalysts"; 1984, *Chemistry Letters*; pp. 2047-2050.

(Continued)

*Primary Examiner*—Paul A Zucker
(74) *Attorney, Agent, or Firm*—Nixon & Vanderhye

(57) ABSTRACT

A product comprising a $C_1$-$C_3$ aliphatic carboxylic acid or corresponding ester is produced by a process comprising carbonylating a $C_1$-$C_3$ aliphatic alcohol or a corresponding ester with carbon monoxide in the presence of a.zeolite catalyst having an 8-member ring channel which is interconnected with a channel defined by a ring with greater than or equal to 8 members, the 8-member ring having a window size of at least 2.5 Angstroms×at least 3.6 Angstroms and at least one Brønsted acid site and the zeolite having a silica:$X_2O_3$ ratio of at least 5, wherein X is selected from aluminium, boron, iron, gallium and mixtures thereof with the proviso that the zeolite is not mordenite or ferrierite.

34 Claims, No Drawings

OTHER PUBLICATIONS

Sardesai, Abhay et al; "Synthesis of Methyl Acetate from Dimethyl Ether Using Group VIII Metal Salts of Phosphotungstic Acid"; 2002, *Energy Sources*, vol. 24, pp. 301-317.

Volkova, G.G., et al; "Heterogeneous catalysts for halide-free carbonylation of dimethyl ether"; 2002, *Catalysts Letters*, vol. 80, No. 3-4, pp. 175-179.

Volkova, G.G., et al; "Solid superacids for halide-free carbonylation of dimethyl ether to methyl acetate"; 2004, *Elsevier B.V.*; 6 pages.

Wegman, Richard W., "Vapour Phase Carbonylation of Methanol or Dimethyl Ether with Metal-ion Exchanged Heteropoly Acid Catalysts"; 1994, *J. Chem. Soc., Chem. Commun.*; pp. 947-948.

Ferrierite—http://www.britannica.com/eb/article?tocId=9034104, 1 page.

Ferrierite-Mg. http://www.mindat.org/min-6931.html, 3 pages.

Ferrierite Mineral Data, http://webmineral.com/data/Ferriente.shtml, 5 pages.

The Mineral Mordenite, http://mineral.galleries.com/galleries.com/minerals/silicate/mordenlt/mordenlt.htm, 2 pages.

Mordenite, http://www.minweb.co.uk/zeolites/morddata.html, 2 pages.

Baerlocher, C., et al; *The Atlas of Zoelite Framework Types*; 5th ed. Elsevier, <?xml:namespace prefix= stI ns="urn:schemas-microsoft-com:office:smarttags" />Amsterdam, 2001—http://www.iza-structure.org/databases/.>?xml:namespace prefix=o ns="urn:schemas-microsoft-com:office:office" />.

Foster, M.D., et al; "A geometric solution to the largest-free-sphere problem in zeolite frameworks"; *Microphorous and Mesoporous Materials*; 90 (2006) pp. 32-38.

Zones, S.I., et al; "Studies on the Role of Fluoride Ion vs Reaction Concentration in Zeolite Synthesis"; *J. Phys. Chem. B.* (2005) 109, pp. 652-661.

Vaughn, D.E.W., et al; "Synthesis of ECR-18—a synthetic analog of paulingite"; *Microporous Mesoporous Mateirals*; 28 (1999), pp. 233-239.

Barri, S.A.I., et al; "Structure of Theta-1, the first unidimensional medium-pore high-silica zeolite"; *Nature*, vol. 312, pp. 533-534 (1984).

Martucci, A., et al; "Crystal structure of zeolite omega, the synthetic counterpart of the natural zeolite mazzite"; *Microporous and Mesoporous Materials*; 63 (2003) pp. 33-42.

Bhat, S.D., et al; "High temperature hydrothermal crystallization, morphology and yield control of zeolite type K-LTL"; *Microphorous and Mesoporous Materials*; 76 (2004) pp. 81-89.

Ko, Y.S., et al; J. Ind. Eng. Chem., vol. 10, No. 4 (2004) pp. 636-644.

Howden, M.G.; "Synthesis of offertite: Part 1. Using various organic compounds as templates"; *Zeolites*; (1987), vol. 7, pp. 255-259.

Howden, M.G.; "Synthesis of offretite: Part 2. Using a combination of tetramethylammonium cations and monoethanolamine or 1,2-diaminoethane as template"; *Zeolites* (1987), vol. 7, pp. 260-264.

Makarova, M.A., et al; "Quantification of Bronsted Acidity in Mordenites"; *Journal of Catalysis*, vol. 172; pp. 170-177 (1997).

PROCESS FOR CARBONYLATION OF ALIPHATIC ALCOHOLS AND/OR ESTER DERIVATIVES THEREOF

BACKGROUND OF THE INVENTION

This invention relates to a process for the selective production of lower aliphatic carboxylic acids and/or their corresponding esters by the carbonylation of the corresponding lower aliphatic alcohol and/or ester derivatives thereof, and, in particular to the selective production of acetic acid and/or methyl acetate by the carbonylation of methanol and/or methyl acetate.

The most widely used industrial process for production of acetic acid is the carbonylation of methanol, which is described generally in British patents 1,185,453 and 1,277,242 and U.S. Pat. No. 3,689,533, for instance. In that type of process, methanol is reacted with carbon monoxide or a carbon monoxide-containing gas in the presence of a rhodium- or iridium-containing catalyst, in the additional presence of a halogen (usually iodine)-containing promoter. Though widely used, nonetheless these processes require the use of expensive corrosion-resistant alloys due to the presence of iodide and result in production of low levels of iodine-containing byproducts that are difficult to remove from the acetic acid by conventional distillation. Some non-halide based catalyst systems have been investigated for this reaction, but none have been commercialized, primarily due to issues with catalyst lifetime and selectivity.

A number of patents describe processes in which methanol or a mixture of methanol and dimethyl ether is carbonylated in the presence of a catalyst. Typically the products are a mixture of acetic acid and methyl acetate, sometimes also including acetic anhydride. In those patents it is disclosed that one of the reactions that may occur is the carbonylation of dimethyl ether to form methyl acetate.

EP-A-0 596 632 discloses the preparation of an aliphatic carboxylic acid by contacting an aliphatic alcohol or a reactive derivative thereof with carbon monoxide in the presence of a copper, nickel, iridium, rhodium or cobalt loaded mordenite zeolite catalyst at high temperatures and pressures.

U.S. Pat. No. 6,387,842 discloses processes and catalysts for converting an alcohol, ether and/or ether alcohol feedstock to oxygenated products by reaction with carbon monoxide in the presence of a catalyst comprising a solid super acid, clay, zeolite or molecular sieve under conditions of temperature and pressure.

WO 2005/105720 discloses a process for the preparation of an aliphatic carboxylic acid, ester or anhydride thereof by contacting an aliphatic alcohol and/or a reactive derivative thereof with carbon monoxide in the presence of a copper, nickel, iridium, rhodium or cobalt loaded mordenite catalyst which has as framework elements, silicon, aluminium and also one or more of gallium, boron and iron.

BRIEF SUMMARY OF THE INVENTION

This invention comprises a process for the selective production of a $C_1$-$C_3$ aliphatic carboxylic acid such as acetic acid and/or the corresponding $C_1$-$C_3$ ester, such as methyl acetate by carbonylating the corresponding $C_1$-$C_3$ aliphatic alcohol, such as methanol and/or an ester thereof, such as methyl acetate with carbon monoxide in the presence of a catalyst comprising a zeolite, having at least one 8-member ring channel, said 8-member ring channel being interconnected with a channel defined by a ring with greater than or equal to 8 members, said 8-member ring having a window size of at least 2.5 Angstroms×at least 3.6 Angstroms and at least one Brønsted acid site and wherein the zeolite has a silica:$X_2O_3$ ratio of at least 5, wherein X is selected from aluminium, boron, iron, gallium and mixtures thereof, with the proviso that the zeolite is not mordenite or ferrierite.

DETAILED DESCRIPTION OF THE INVENTION

This invention comprises a process for the selective production of a $C_1$-$C_3$ aliphatic carboxylic acid such as acetic acid and/or the corresponding ester, such as methyl acetate by carbonylating the corresponding $C_1$-$C_3$ aliphatic alcohol, such as methanol and/or an ester derivative thereof, such as methyl acetate with carbon monoxide in the presence of a catalyst comprising a zeolite having at least one 8-member ring channel, said 8-member ring channel being interconnected with a channel defined by a ring with greater than or equal to 8 members, said 8-member ring having a window size of at least 2.5 Angstroms×at least 3.6 Angstroms and at least one Brønsted acid site and wherein the zeolite has a silica:$X_2O_3$ ratio of at least 5, wherein X is selected from aluminium, boron, iron, gallium and mixtures thereof, with the proviso that the zeolite is not mordenite or ferrierite.

One component of the feed to the process may be a $C_1$-$C_3$ aliphatic alcohol. The process is particularly applicable to alcohols such as methanol, ethanol and n-propanol. A preferred alcohol is methanol. Alternatively, an ester of the alcohol may be employed as the feed, such as methyl acetate or ethyl acetate. A mixture of the alcohol and its ester derivative may be employed, such as a mixture of methanol and methyl acetate.

Where an alcohol is used as the feed to the process, the product will be dependent upon the degree of conversion of the alcohol. If the conversion is 100% then the product will be the corresponding carboxylic acid. Thus where methanol is the alcohol feed, the product will comprise acetic acid. If the conversion is less than 100%, the alcohol will be converted to a mixture of the corresponding carboxylic acid and carboxylic acid ester. If the ester employed as the feed, is a symmetrical ester, for example, methyl acetate, the main product of the carbonylation process will be the corresponding carboxylic acid (in this case, acetic acid). If the ester is asymmetrical, then the product will comprise a mixture of carboxylic acids formed from each of the alkyl groups of the ester.

A second component of the process is a feed comprising carbon monoxide. The feed may comprise substantially pure carbon monoxide (CO), for example, carbon monoxide typically provided by suppliers of industrial gases, or the feed may contain impurities that do not interfere with the conversion of the alkyl ether to the desired ester, such as hydrogen, nitrogen, helium, argon, methane and/or carbon dioxide. For example, the feed may comprise CO that is typically made commercially by removing hydrogen from synthesis gas via a cryogenic separation and/or use of a membrane.

The carbon monoxide feed may contain substantial amounts of hydrogen. For example, the feed may be what is commonly known as synthesis gas, i.e. any of a number of gaseous mixtures that are used for synthesizing a variety of organic or inorganic compounds, and particularly for ammonia synthesis. Synthesis gas typically results from reacting carbon-rich substances with steam (in a process known as steam reforming) or with steam and oxygen (a partial oxidation process). These gases contain mainly carbon monoxide and hydrogen, and may also contain smaller quantities of carbon dioxide and nitrogen. Suitably, the ratio of carbon monoxide:hydrogen may be in the range 1:3 to 15:1 on a molar basis, such as 1:1 to 10:1. The ability to use synthesis gas provides another advantage over processes for producing acetic acid from methanol, namely the option of using a less expensive carbon monoxide feed. In methanol-to-acetic acid processes, the inclusion of hydrogen in the feed can result in production of unwanted hydrogenation.

The catalyst for use in the process of the invention is a zeolite, excluding mordenite and ferrierite. Zeolites, both natural and synthetic are microporous crystalline aluminosilicate materials having a definite crystalline structure as determined by X-ray diffraction. The chemical composition of zeolites can vary widely but they typically consist of $SiO_2$ in which some of the Si atoms may be replaced by tetravalent atoms such as Ti or Ge, by trivalent atoms such as Al, B, Ga, Fe or by bivalent atoms such as Be, or by a combination thereof. A zeolite is comprised of a system of channels which may be interconnected with other channel systems or cavities such as side-pockets or cages. The channel systems are uniform in size within a specific zeolite and may be three-dimensional but are not necessarily so and may be two-dimensional or one-dimensional. The channel systems of a zeolite are typically accessed via 12-member rings, 10-member rings or 8 member rings. The zeolites for use in the present invention contain at least one channel which is defined by an 8-member ring. Preferred zeolites are those which do not have side-pockets or cages within the zeolite structure. The *Atlas of Zeolite Framework Types* (C. Baerlocher, W. M. Meier, D. H. Olson, $5^{th}$ ed. Elsevier, Amsterdam, 2001) in conjunction with the web-based version (http://www.iza-structure.org/databases/) is a compendium of topological and structural details about zeolite frameworks, including the types of ring structures present in the zeolite and the dimensions of the channels defined by each ring type. For the purposes of the present invention, the term 'zeolite' also includes materials having a zeolite-type structure such as delaminated porous crystalline oxide materials and pillared layered oxide materials such as ITQ-36.

The process of the present invention employs a zeolite having at least one channel defined by an 8-member ring of tetrahedrally co-ordinated atoms (tetrahedra) with a window size having a minimum dimension of 2.5 Angstroms×3.6 Angstroms. The 8-member ring channel is interconnected with at least one channel defined by a ring with equal to or greater than 8 members, such as 10 and/or 12 members. The interconnected 8-, 10-, and 12-member ring channels provide access to Brønsted acid sites contained in the 8-member ring channels to enable the carbonylation reaction to proceed at acceptable rates.

The zeolite for use in the present invention may consist of interconnected channels defined solely by 8-member rings, such as zeolites of framework type CHA, for example, chabazite and framework type ITE, for example ITQ-3. Preferably, however, the zeolite has at least one channel formed by an 8-member ring and at least one interconnecting channel defined by a ring with greater than 8 members, such as a 10, and/or 12 member ring. Non-limiting examples of zeolites having 8-member ring channels and interconnecting larger ring channel systems include zeolites of framework type OFF, for example, offretite, GME, for example Gmelinite, MFS, such as ZSM-57, EON such as ECR-1 and ETR such as ECR-34. Preferably, the zeolites for use in the process of the present invention have at least one 8-member ring channel interconnected with at least one 12-member ring channel, such as those of framework type OFF and GME, for example, offretite and gmelinite.

However, the mere presence of an interconnected 8-member ring channel in a zeolite is not sufficient to develop an effective carbonylation process. The window size of the channel systems also has to be controlled such that the reactant molecules can diffuse freely in and out of the zeolite framework. It has now been found that effective carbonylation can be achieved if the aperture (pore width) of an 8-member ring channel of the zeolite has a minimum dimension of 2.5×3.6 Angstroms. Channel dimensions of zeolite framework types may be found, for example, in the *Atlas of Zeolite Framework Types*. In addition, M. D. Foster, I. Rivin, M. M. J. Treacy and O. Delgado Friedrichs in "A geometric solution to the largest-free-sphere problem in zeolite frameworks" Microporous and Mesoporous Materials 90 (2006) 32-38, have used Delaunay triangulation methods applied to known zeolite frameworks and have tabulated the largest free-sphere diameters for diffusion along the three principal crystallographic directions for the 165 zeolite frameworks that are currently listed in the *Atlas of Zeolite Framework Types*. Ring window sizes may be modified by suitable atomic substitutions that change bond lengths and bond angles of the tetrahedrally co-ordinated atoms and the bridging oxygens.

A partial listing of zeolite framework types having at least one interconnected 8 member ring channel of minimum dimension of 2.5×3.6 Angstroms taken from *The Atlas of Zeolite Framework Types* is given below:

| MOR | Mordenite | 12 (6.5 × 7.0 Å) | 8 (3.4 × 4.8 Å) | 8 (2.6 × 5.7 Å) |
|-----|-----------|------------------|-----------------|-----------------|
| OFF | Offretite | 12 (6.7 × 6.8 Å) | 8 (3.6 × 4.9 Å) | |
| FER | Ferrierite | 10 (4.2 × 5.4 Å) | 8 (3.5 × 4.8 Å) | |
| CHA | Chabazite | 8 (3.8 × 3.8 Å) | | |
| ITE | ITQ3 | 8 (3.8 × 4.3 Å) | 8 (2.7 × 5.8 Å) | |
| GME | Gmelinite | 12 (7.0 × 7.0 Å) | 8 (3.6 × 3.9 Å) | |
| ETR | ECR-34 | 18 (10.1 Å) | 8 (2.5 × 6.0 Å) | |
| MFS | ZSM-57 | 10 (5.1 × 5.4 Å) | 8 (3.3 × 4.8 Å) | |
| EON | ECR-1 | 12 (6.7 × 6.8 Å) | 8 (3.4 × 4.9 Å) | 8 (2.9 × 2.9 Å) |

Zeolites are available from commercial sources. Alternatively they may be synthesized using known techniques. In general, synthetic zeolites are prepared from aqueous reaction mixtures comprising sources of appropriate oxides. Organic directing agents may also be included in the reaction mixture for the purpose of influencing the production of a zeolite having the desired structure. After the components of the reaction mixture are properly mixed with one another, the reaction mixture is subjected to appropriate crystallization conditions. After crystallization of the reaction mixture is complete, the crystalline product may be recovered from the remainder of the reaction mixture. Such recovery may involve filtering the crystals, washing with water followed by a calcination treatment at high temperature. The synthesis of zeolites is described in numerous references. For example, zeolite Y and its synthesis is described in U.S. Pat. No. 3,130,007, zeolite ZSM-23 is described in U.S. Pat. No. 4,076,842 and J. Phys. Chem. B, 109, 652-661 (2005), Zones, S. I. Darton, R. J., Morris, R and Hwany, S-J; ECR-18 is described in Microporous Mesoporous Mat., 28, 233-239 (1999), Vaughan D. E. W. & Strohmaier, K. G.; Theta-1 is described in Nature, 312, 533-534 (1984). Barri, S. A. I., Smith W. G., White, D. and Young, D.; Mazzite is described in Microporous Mesoporous Mat., 63, 33-42 (2003), Martucci, A, Alberti, A, Guzmar-Castillo, M. D., Di Renzo, F. and Fajula, F.; Zeolite L is described in Microporous Mesoporous Mat., 76, 81-99 (2004), Bhat, S. D., Niphadkair, P. S., Gaydharker, T. R., Awate, S. V., Belhekar, A. A. and Joshi, P. N and also in J. Ind. Eng. Chem. Vol. 10, No. 4 (2004), 636-644, Ko Y. S, Ahn W. S and offretite is described in Zeolites 255-264, Vol. 7, 1987 Howden M. G.

The zeolite catalyst for use in the process of the present invention is used in the acid form, generally referred to as the 'H' form of the zeolite, for example, H-offretite. Other forms of the zeolite, such as the $NH_4$ form can be converted to the H-form, for example, by calcining the $NH_4$ form at elevated temperature. The acid form of a zeolite will possess Brønsted acid ($H^+$) sites which are distributed among the various channel systems in the zeolite. For example, H-offretite has $H^+$ sites located in the 12 member ring channels and in the 8 member ring channels. The number or concentration of $H^+$ species residing in any particular channel system can be determined by known techniques such as infra-red NMR spectroscopic techniques. Quantification of Brønsted acidity by FTIR and NMR spectroscopy is described, for example, in Makarova, M. A., Wilson, A. E., van Liemt, B. J., Mesters, C. de Winter, A. W., Williams, C. Journal of Catalysis 1997, 172, (1), 170. The two types of channels in H-offretite (defined by 12 member rings and 8 member rings) give rise to at least two bands associated with the hydroxyl region of H-offretite, one corresponding to vibration into the larger pores and the other, at a lower frequency, vibrating into the smaller pores. Work by the present inventors has shown that there is a correlation between the number of $H^+$ sites located in an 8-member ring channel and the carbonylation rate whereas no such correlation has been observed for 12-member ring channels. It has been found that carbonylation rates increase in parallel with the number of $H^+$ sites within 8 member ring channels. In contrast, no correlation is evident with the number of $H^+$ sites within 12 member ring channels. The number of $H^+$ sites within 8-member ring channels can be controlled by replacement of the $H^+$ with metal cations such as $Na^+$ or $Co^{2+}$ using known ion-exchange techniques.

The chemical composition of a zeolite may be expressed as involving the molar relationship:

$$SiO_2:X_2O_3$$

wherein X is a trivalent element, such as aluminium, boron, iron and/or gallium, preferably aluminium. The $SiO_2:X_2O_3$ ratio of a given zeolite is often variable. For example, it is known that offretite can be synthesized with $SiO_2:Al_2O_3$ ratios of 6 to 90 or greater, zeolite Y, from about 1 to about 6, chabazite from about 2 to 2000 and gmelinite may be synthesised with $SiO_2:Al_2O_3$ ratios of greater than 4. In general, the upper limit of the $SiO_2:X_2O_3$ ratio is unbounded, for example, the zeolite ZSM-5. The zeolites for use in the present invention have a $SiO_2:X_2O_3$ molar ratio of at least 5, preferably in the range 7 to 40, such as 10 to 30. Suitably, the $SiO_2:X_2O_3$ molar ratio is less than or equal to 100. Particular $SiO_2:X_2O_3$ ratios can be obtained for many zeolites by dealumination (where X is Al), by standard techniques using high temperature steam treatment or acid washing.

In the carbonylation of an alcohol or ester, such as methanol and methyl acetate, water is generated in-situ. For example, where an alcohol is used as the feed, water is generated by the dimerisation of the alcohol to an ether, Water may also be generated by the esterification of the alcohol with the carboxylic acid product. Water may be fed separately or together with the alcohol or ester feed component or a mixture thereof. The water may be present in liquid or vapour form.

In general, the process is run at temperatures above about 250° C., that is, at temperatures of from about 250 to about 400° C., preferably from about 275 to about 350° C.

Typical total operating pressures are from about 1 bar to about 100 bar, preferably with carbon monoxide pressures greater than 10 bar and reactant pressures below 5 bar.

The process may be run as either a continuous or a batch process, with continuous processes typically preferred. Essentially, the process is a gas-phase operation, with reactants being introduced in either liquid or gaseous phase and products withdrawn as gases. As desired, the reaction products may subsequently be cooled and condensed. The catalyst may be used as convenient, in either a fixed bed or a fluidized bed. In operating the process, unreacted starting materials may be recovered and recycled to the reactor. Where the product is methyl acetate it may be recovered and sold as such, or may be forwarded to other chemical process units as desired. If desired, the entire reaction product may be sent to a chemical process unit for conversion of the carboxylic acid and/or ester products such as methyl acetate or acetic acid to other useful products.

In one embodiment of the invention, where methyl acetate is a product, it may be recovered from the reaction products and contacted with water to form acetic acid via hydrolysis reactions. Alternatively, the entire product may be passed to a hydrolysis step, and acetic acid separated thereafter. The hydrolysis step may be carried out in the presence of an acid catalyst, and may take the form of a reactive distillation process, well known in the art.

In another embodiment, the hydrolysis of an ester product to alcohol and carboxylic acid is performed by injecting water at one or more points in the catalyst bed, once a significant amount of ester has been produced by carbonylation.

The following examples are presented as illustrative of the invention. However, they are not meant to limit the scope of this invention.

GENERAL PROCEDURES

To investigate the catalytic activity of zeolites for non-iodide carbonylation of methanol to acetic acid the zeolites can be tested in a pressure flow reactor in accordance with the following procedure. Zeolite pellets of size 500-1000 um are loaded into a pressure flow reactor. A catalyst pre-bed is also employed to ensure efficient mixing/heating of the reactants. The pre-bed is gamma-alumina which allows methanol to form a methanol/dimethylether/water equilibrium. The catalysts are activated under flowing nitrogen (100 cm3/min) at 350° C. for 16 hrs and then reduced under carbon monoxide (200 cm3/min) at 350° C. for 2 hours. The system is then pressurised up to 30 barg using a back pressure regulator. The flow rate of the carbon monoxide is adjusted to 400 cm3/min (GHSV=2200) and methanol is fed to the reactor via a pump (rate+0.15 ml/min). The liquid products and unconverted reactants are collected in a cooled trap, while gaseous products and un-reacted feeds are sampled downstream by an online gas chromatograph. The reaction is sampled at frequent intervals and the liquid products analysed off line using gas-chromatography. Using zeolite H-Offretite (silica:alumina molar ratio of 10) as the catalyst in the above described carbonylation of methanol, it would be expected that significant amounts of both methyl acetate and acetic acid would be seen in the liquid products. Similarly, if zeolite H-Gmelinite (silica:alumina molar ratio of 8) was employed as the catalyst in the above described carbonylation of methanol, it would be expected that significant amounts of both methyl acetate and acetic acid would be seen in the liquid products. Both offretite and gmelinite zeolites have 8-member ring channels intersecting with 12-member ring channels. In comparison, it would be expected that if zeolite H-ZSM-5 (silica:alumina ratio of 23; 10-member ring channels only) or zeolite H-Y (silica:alumina ratio of 12; 12-member ring channels only)

were employed as the catalyst, only trace amounts of acetic acid would be seen in the liquid product.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A process for the production of a $C_2$-$C_4$ aliphatic carboxylic acid and/or the corresponding ester, by carbonylating the corresponding $C_1$-$C_3$ aliphatic alcohol and/or an ester derivative thereof with carbon monoxide in the presence of a catalyst comprising a zeolite having at least one 8-member ring channel, said 8-member ring channel being interconnected with a channel defined by a ring with greater than or equal to 8 members, said 8-member ring having a window size of at least 2.5 Angstroms×at least 3.6 Angstroms and at least one Brønsted acid site and which zeolite has a silica:$X_2O_3$ molar ratio of at least 5, wherein X is selected from aluminium, boron, iron, gallium and mixtures thereof with the proviso that the zeolite is not mordenite or ferrierite.

2. A process according to claim 1 in which the $C_2$-$C_4$ carboxylic acid is acetic acid and the corresponding ester is methyl acetate.

3. A process according to claim 1 wherein the $C_1$-$C_3$ alcohol is methanol or ethanol.

4. A process according to claim 3 wherein the aliphatic alcohol is methanol.

5. A process according to claim 1 wherein the ester derivative of the alcohol is methyl acetate.

6. A process according to claim 1 wherein the product of the carbonylation reaction is an ester.

7. A process according to claim 1 in which the temperature is from about 250° C. to about 400° C.

8. A process according to claim 1 in which the temperature is from about 275° C. to about 350° C.

9. A process according to claim 1 in which the catalyst comprises a fixed bed of catalyst.

10. A process according to claim 1 in which the catalyst comprises a fluidized bed of catalyst.

11. A continuous process according to claim 1.

12. A batch process according to claim 1.

13. A process according to claim 1 in which the carbon monoxide-containing feed further comprises hydrogen.

14. A process according to claim 13 in which the carbon monoxide-containing feed comprises a synthesis gas.

15. A process according to claim 6 comprising further hydrolyzing the ester product to produce the corresponding carboxylic acid.

16. A process according to claim 15 in which the hydrolysis is conducted in a separate reactor from the ester-producing reaction.

17. A process according to claim 15 in which the hydrolysis is conducted in the same reactor as the ester-producing reaction.

18. A process according to claim 1 in which the zeolite catalyst is selected from the group consisting of a zeolite of framework type OFF, CHA, ITE, GME, ETR, EON, and MFS.

19. A process according to claim 18 wherein the catalyst is selected from the group consisting of offretite, gmelinite, ZSM-57 and ECR-18.

20. A process according to claim 19 wherein the zeolite is offretite.

21. A process according to claim 1 wherein the catalyst consists of channels defined solely by 8-member rings.

22. A process according to claim 1 wherein the channel defined by the 8-member ring interconnects with at least one channel defined by a ring with greater than 8 members.

23. A process according to claim 22 wherein the at least one channel defined by a ring with greater than 8 members is defined by a ring having 10 or 12 members.

24. A process according to claim 23 wherein the at least one channel defined by a ring with greater than 8 members is defined by a ring having 12 members.

25. A process according to claim 1 wherein the silica:$X_2O_3$ ratio is less than or equal to 100.

26. A process according to claim 1 wherein the silica:$X_2O_3$ ratio is in the range 7 to 40.

27. A process according to claim 1 wherein the silica:$X_2O_3$ ratio is in the range 10 to 30.

28. A process according to claim 1 wherein X is selected from aluminium, gallium and mixtures thereof.

29. A process according to claim 1 wherein X is aluminium.

30. A process according to claim 1 wherein X is aluminium and the silica:$Al_2O_3$ ratio is less than or equal to 100.

31. A process according to claim 30 wherein the silica:$Al_2O_3$ ratio is in the range 7 to 40.

32. A process according to claim 31 wherein the silica:$Al_2O_3$ ratio is in the range 10 to 30.

33. A process according to claim 1 wherein water is also fed to the carbonylation reaction.

34. A process according to claim 33 wherein the water is fed together with or separately to the alcohol and ester feed.

* * * * *